United States Patent [19]

Barker et al.

[11] 4,069,104

[45] Jan. 17, 1978

[54] CONVERSION OF ALDOSE TO KETOSE IN THE PRESENCE OF OXYANIONS OR MIXED OXYANIONS OF TIN OR GERMANIUM

[75] Inventors: Sidney Alan Barker; Peter John Somers; Robin Ross Woodbury, all of Birmingham; Geoffrey Harry Stafford, Stockton-on-Tees, all of England

[73] Assignee: Imperial Chemical Industries Limited, London, England

[21] Appl. No.: 696,950

[22] Filed: June 17, 1976

[30] Foreign Application Priority Data

June 17, 1975 United Kingdom ............... 25757/75

[51] Int. Cl.$^2$ ..................... C12D 13/02; C13K 11/00; C13K 13/00; C07H 3/02
[52] U.S. Cl. ................... 195/31 F; 127/46 A; 195/31 R; 195/114; 536/1; 536/121
[58] Field of Search .................... 195/114, 31 F, 31 R, 195/116, 117, 12, 115; 127/46 R, 42, 46 A; 536/121, 1

[56] References Cited

U.S. PATENT DOCUMENTS

| 3,095,329 | 6/1963 | Giesen et al. .................... 127/55 |
| 3,206,375 | 9/1965 | Kinoshita et al. ................... 195/31 F |
| 3,689,362 | 9/1972 | Tukasaki ............................ 195/31 F |
| 3,935,069 | 1/1976 | Long ................................. 195/31 F |

OTHER PUBLICATIONS

Takasaki, "Studies on Sugar-isomerizing Enzymes", Agr. Biol. Chem., vol. 35, No. 9, (1971), pp. 1371–1375.
Antikainen, "Spectropolarimetric Studies on Chelate Formation II, Chelation of the Germanate Ion with Fructose in Aqueous Alkaline Solutions", Chem. Abstracts, vol. 82, No. 7, (1975), p. 465 NBS# 43669k.

Primary Examiner—Raymond N. Jones
Assistant Examiner—Thomas G. Wiseman
Attorney, Agent, or Firm—Cushman, Darby & Cushman

[57] ABSTRACT

A process for converting aldoses or derivatives thereof into ketoses or derivatives thereof which takes place in the presence of oxyanions or mixed complex oxyanions of germanium or tin which form stronger complexes with the ketoses or derivatives thereof than with the aldoses or derivatives thereof. Using the process the equilibrium position in the aldose-ketose reaction is shifted towards higher proportions of ketose. The process is very applicable to the conversion of glucose to fructose particularly when this conversion takes place enzymatically in the presence of glucose isomerase.

18 Claims, 2 Drawing Figures

CONVERSION OF ALDOSE TO KETOSE IN THE PRESENCE OF OXYANIONS OR MIXED OXYANIONS OF TIN OR GERMANIUM

This invention relates to a process for the conversion of an aldose or aldose derivative to a ketose or ketose derivative in the presence of an oxyanion and in particular to the conversion of glucose to fructose, mannose to fructose, glucose 6-phosphate to fructose 6-phosphate, maltose to maltulose, galactose to tagatose, and lactose to lactulose and to other analogous reactions such as the conversion of xylose to xylulose. The process can be carried out in the presence or absence of an enzyme catalysing the conversion.

When the conversion of glucose to fructose is conducted in the presence of an enzyme, glucose isomerase, equilibrium is very often reached when 50 to 55% of the glucose in the reaction medium has been converted to fructose. Hitherto it has not been possible to convert glucose to fructose by a non-enzymic reaction without the production of by-products. There are numerous publications, for example U.S. Pat. Nos. 2,487,121, 3,432,345, 3,558,355 and 3,514,327 and German Pat. No. 1,163,307, relating to non-enzymic conversion of glucose to fructose all of which describe processes in which the fructose produced is accompanied by alkaline degradation and other products arising from the purely chemical and non-enzymic reaction. Because of this any large scale production of fructose up to the present has been based on an enzyme catalysed reaction.

In the enzymic conversion process as the proportion of fructose in the enzymic reaction medium increases, the rate of the reaction whereby fructose is produced decreases. Therefore in a commercial process for converting glucose to fructose the fructose yield is optimised by balancing a loss in fructose production against the decreasing reaction rate whereby the proportion of fructose in the reaction medium can be increased. A commercially operated process may be optimised to produce a syrup in which typically 40% of glucose has been converted to fructose. In most chemical non-enzymic conversions of glucose to fructose, the amount of fructose present drops after reaching a maximum.

Clearly it is advantageous to increase the proportion of glucose which can economically be converted to fructose during the reaction.

This can be achieved by the effective removal of fructose from the reaction medium by the inclusion in the medium of a reagent which forms a stronger complex with fructose than with glucose although the complexing agent may have additional properties that increase or decrease the reaction rate. Reagents which have been proposed for this purpose are borate compounds — see Y Takasaki, Agr Biol Chem 1971, 35(9), 1371–5 and USP 3,689,362 (enzymic reaction) and J F Mendicino, J Amer Chem Soc 82, 1960, 4975 (chemical reaction). Also arene boronates have been proposed by S A Barker, P J Somers and B W Hatt in UK Specification No 1,369,185 for both chemical and enzymic reactions. Disadvantages of these prior proposals are, in the case of borate compounds, that these are toxic and could constitute a health hazard in a product intended for use as a sweetener in foodstuffs for human consumption and, in the case of benzene boronate it has a limiting solubility, cannot form complexes with a 2:1 ratio of sugar: boronate and high concentrations of fructose in the product cannot be attained at high sugar concentrations ( S A Barker, B W Hatt and P J Somers, Carbohydrates Res, 26 (1973) 41–53). Thus these complexing reactions do not lend themselves readily to use in commercially operated conversion processes. In order to develop a commercial process in which the proportion of fructose in the syrup produced is increased it is necessary to find a complexing reagent which does not have such disadvantages associated with its use.

According to the present invention we provide a process for the conversion of an aldose or an aldose derivative to a ketose or ketose derivative wherein the conversion takes place in the presence of a complexing reagent which is an oxyanion or mixed complex oxyanion of germanium or tin which forms a stronger complex with the ketose or ketose derivative than with the aldose or aldose derivative.

Also according to the present invention we provide a process for the conversion of an aldose or aldose derivative to a ketose or ketose derivative wherein the conversion takes place in the presence of a complexing agent which is an oxyanion or mixed complex oxyanion of germanium which forms a stronger complex with the ketose or ketose derivative than with the aldose or aldose derivative.

Very suitably the aldose derivative is an aldose phosphate or a glycosyl derivative of an aldose.

Whilst the invention is applicable to a wide range of conversions and in particular to those conversions specified hereinabove it is most usefully employed in the conversion of glucose to mannose to fructose. During a conversion an enzyme catalyst may be present where this enables milder reaction conditions to be employed or has other advantages such as the selective action of the enzyme employed on only one isomer (D or L) of the aldose or aldose derivative. When an enzyme-catalysed conversion is carried out the enzyme may be present in solution or in an immobilised form on a solid matrix that may be a living cell, an inactivated cell or any other suitable support. The enzyme may also be in soluble form. The isomerase-type enzyme suitable for conversions of the type (examples listed in Table A) to which the invention is applicable may constitute one or more of a series of enzymes engaged in sequential reactions.

TABLE A

| | Conversion | | Enzyme | Reference |
|---|---|---|---|---|
| 1 | D-galactose | ⇌ D-tagatose | L-arabinose isomerse (D-galactose isomerase) | J Biol Chem, 1971, 246, 5102–6 |
| 2 | L-arabinose | ⇌ L-ribulose | As in 1 | As in 1 |
| 3 | L-fucose | ⇌ L-fuculose | L-fucose isomerase (D-arabinose isomerase) | J Biol Chem, 1958, 230, 457 |
| 4 | L-rhamnose | ⇌ L-rhamulose | L-rhamnose isomerase | Methods Enzymol, 9, 597–82, (1966) |
| 5 | L-mannose | ⇌ L-fructose | L-mannose isomerase | Carb Res, 1968, 8, 3444 |
| 6 | D-mannose | ⇌ D-fructose | D-lyxose isomerase (D-mannose isomerase) | J Biol Chem, 218 (1956) 535 |

TABLE A-continued

| | Conversion | | Enzyme | Reference |
|---|---|---|---|---|
| 7 | D-glucose | ⇌ D-fructose | D-glucose isomerase (D-xylose isomerase) | Biochem Biophys Acta, (1969) 178, 376–9 |
| 8 | D-glycero-D-manno-heptose | ⇌ D-sedoheptulose | As in 6 | J Biol Chem, 218, (1956) 535 |
| 9 | D-lycose | ⇌ D-xylulose | As in 6 | As in 6 |
| 10 | D-xylose | ⇌ D-xylulose | As in 7 | As in 7 |
| 11 | L-xulose | ⇌ L-xylulose | L-xylose isomerase | Fed Proc, 19 (1960) 82 |
| 12 | D-arabinose | ⇌ D-ribulose | As in 3 | As in 3 |
| 13 | D-ribose 5-phosphate | ⇌ D-ribulose 5-phosphate | D-ribose-5-phosphate isomerase | J Biol Chem, 1957, 226 65 |
| 14 | D-arabinose 5-phosphate | ⇌ D-ribulose 5-phosphate | D-arabinose 5-isomerase | Methods Enzymol, 9, 585–8 (1966) |
| 15 | D-glyceraldehyde-3-phosphate | ⇌ Dihydroxy acetone 3-phosphate | Triose phosphate isomerase | Biochem J, 1968, 107, 775 |
| 16 | D-galactose 6-phosphate | | D-tagotose 6-phosphate | D-galactose-6-6-phosphate isomerase | Biochem Biophys Res Comm, 1973, 52, 641–7 |
| 17 | D-glucose 6-phosphate | | D-fructose 6-phosphate | D-Glucose-6-phosphate isomerase | J Biol Chem, 1973, 248, 2219 |
| 18 | D-mannose 6-phosphate | | D-fructose 6-phosphate | D-mannose-6-phosphate isomerase | J Biol Chem, 1968, 243, 5410–19 |
| 19 | D-glucosamine 6-phosphate | | D-fructose 6-phosphate | D-fucosamine-6-phosphate isomerase | Adv Enzymol, 43, 491, (1975) |

In this specification the term ketose is to be understood to mean a ketulose, see the discussion of the nomenclature of ketoses in "The Editorial Report on Nomenclature," Journal of the Chemical Society P 5110, 1952).

The complexing reagent may be introduced into the conversion process in any suitable manner, eg as an aldose-oxyanion complex or a derivative of an aldose cyanion complex or as a salt or as a compound such as an oxide which forms oxyanions or mixed complex cyanions under the conditions of the conversion process. The complexing reagent may also be introduced as an oxyanion which was previously held on a polyol or an ion exchange resin or other insoluble support that chelates with the complexing reagent or has the complexing reagent as a counter ion.

Suitably the mixed complex oxyanion is one formed by the interaction of an oxyanion of germanium or tin with an ion of another Group IV element or of an element from Group V or VI. Preferably the oxyanion or mixed complex oxyanion contains germanium. Particularly suitable complexing reagents are germanate or poly-germanate ions, included in the process as for example sodium germanate or germanium dioxide, and used in solution, as immobilised chelates or as counter ions of ion exchange resins. Mixed ions such as [Ge $O_2$ $O_4)_2]^{2-}$ [HGe $O_2$ $(PO_4)]^{2-}$ or lactate-germanium species may be advantageously employed in some cases.

It is known from Lindberg and Swan, Acta Chem Scand, 14, (1960), 1043–50, that when separated by electrophoresis at pH 10.7 fructose-germanate complexes are very different from glucose-germanate complexes, and the former have more than twice the mobility of the latter at 40° C. V A Nazarenko and G V Lyantikova (Zh Neorgan Khim, 8 (1963) 2271, 1370) give ionization constants for glucose and fructose with germanate of $8.3 \times 10^{-6}$ and $1.04 \times 10^{-4}$ respectively. They further cite instability constants for glucose and fructose with germanate of $3.54 \times 10^{-2}$ and $4.24 \times 10^{-5}$ respectively.

It is surprising that germanate ions should be useful as agents in the conversion of glucose to fructose for the following reasons 1. It has been shown that germanate exists as a monogermanate ⇌ pentagermanate ⇌ heptagermanate equilibrium which is displaced to the right on increasing the germanium concentration and to the left by increasing the pH above pH 9 (D A Everest and J C Harrison, J Chem Soc, 1959, p 2178–2182). For an economic process it is preferred to have the minimum weight of germanate species for the maximum conversion rate as well as avoiding the production of alkaline degradation byproducts. 2. Germanium dioxide and sodium germanate have a very limited solubility in water - see P J Antikainen (Suomen Kenustilehti, 33B (1960) 38–40). Gulzian and Muller, J Amer Chem Soc, 1932, 54, 3142 quote 31–33 mM for $GeO_2$ in water. D A Everest and J C Harrison, J Chem Soc, 1959, 2178, quote 870 mM for sodium germanate. 3. Magnesium ions are generally present in the reaction media used in glucose to fructose enzymic conversions. Magnesium ortho germanate ($Mg_2GeO_4$) is extremely insoluble in water and is used in the analytical determination of germanium — see J H Muller, J Amer Chem Soc, 1922 p 2493–2498. Under the conditions cited below it did not precipitate out of solution. 4. Glucose isomerase has a steric requirement for -D-glucose (K J Schray and I A Rose, Biochemistry 10 (1971) 1058–1062) and the glucose-germanate complex known to be formed could have interfered with the enzyme reaction by inhibiting it partially or wholly. Indeed the 1,2 cis glycol of α-D-glucose is suitable for complexing with germanate rather than α-D-glucose. 5. Mannose complexes more strongly than glucose with germanate (P J Antikainen, Acta Chem Scand., 13 (1959) 312).

The conversion of glucose to fructose may be performed by a purely chemical reaction using the germanate species or stannate complex to displace the pseudo equilibria described by S A Barker, B W Hatt and P J Somers (Carb Res, 26 (1973) 41–53). Preferably however it is performed as an enzyme catalysed reaction in the presence of glucose isomerase. Any glucose isomerase enzyme may be used in the conversion but these enzymes vary as to their optimum pH and temperature. Suitable isomerases include those derived from bacteria of the genera Aerobactor, Pseudomonas, Lactobacillus (K Yamanaka, Agr Biol Chem, 27, 1963, 265–270) Streptomyces, Curtobacterium (as described in our co-pending UK Application No 13994/74), or, particularly, Arthrobacter (as described in UK Specification No 1,328,970). Glucose isomerases from the thermophilic microorganisms of the genera Thermoactinomyces, Thermopolyspora, Thermomonospora and Pseudonocardia such as are described in Japanese Patent Publication No. 74/30588 are also suitable. Some of the above glucose isomerases have a requirement for cobalt ions for optimum activity.

The conversion of glucose to fructose may be performed continuously by passing a solution containing glucose through a column containing the immobilised enzyme or other catalyst. Preferably the enzyme is immobilised by being contained in flocculated whole microbial cells in the manner described in UK Pat. Specification No. 1,368,650. The complexing reagent, eg germanate or stanate species, may be present in the solution passed into the column or with the immobilised enzyme or other catalyst in the column. In the latter case the column may be packed with immobilised enzyme or other catalyst having the reagent admixed with it and homogeneously dispersed throughout the column or alternatively the column may contain alternate layers of immobilised enzyme or other catalyst and reagent separated by meshes or grids. When the reagent is present in the column it is in an insoluble form, for example in gel form, as a zeolite or as an inorganic or organic polymeric derivative.

After a glucose to fructose conversion fructose can be separated from the mixture containing the complexing reagent and removed from the process either alone or in admixture with glucose. The product of the process is fructose, a glucose/fructose syrup or both fructose and a glucose/fructose syrup. The complexing agent alone, together with glucose or together with glucose and complexed glucose can be recycled. Separation and recycling may be performed by any suitable method. Two particularly suitable methods for separation and recycling are as follows:

a. A method wherein the initial product of the glucose/fructose conversion is passed through a column containing a cation exchange resin with cationic counterions of a metal selected from Group II of the Periodic Table and hydrogen ions. This divides the initial product into fructose which is removed as the final product of the process and glucose plus the complexing reagent which is recycled.

Preferably the Group II metal ions are calcium ions.

b. A method wherein the initial product of the glucose/fructose conversion is passed first through a column containing a cationic exchange resin with cationic counterions of a metal of Groups I or II of the Periodic Table, preferably sodium ions. This divides the initial product into two parts namely (i) a syrup containing glucose and fructose and (ii) fructose plus the complexing reagent. Part (i) is removed whilst part (ii) is passed through a column as described under a) above to separate fructose from the complexing agent which latter is recycled.

In both methods (a) and (b) above the resin is preferably a nuclearly sulphonated polystyrene cation exchange resin containing a cross-linking agent.

Alternatively other methods may be used such as by breaking down the fructose-containing complex using "Borasorb" (Registered Trade Mark) sold by Calbiochem Ltd — a polymer comprising a long chain of cis hydroxyl groups linked through a tertiary N atom to a polystyrene divinylbenzene grid and normally sold to absorb borate — to give fructose and the complexing reagent. If the reaction is conducted with the complexing reagent in solution in the reaction medium this reagent may be also recycled. Thus the germanate absorbed on the "Borasorb" can be eluted with alkali or acid. All these manipulations can be avoided if the complexing reagent (eg germanate) is used in an immobilised form.

The conversion of glucose to fructose is preferably conducted enzymatically and continuously using a column of flocculated whole cells containing the enzyme as described above. When the reagent is present in the reaction medium entering the column it is preferably present in concentrations between 200 mM and 800 mM, especially 500 mM and 600 mM. The reaction medium entering the column preferably contains 30% w/w to 50% w/w glucose in aqueous solution and the reaction is conducted in such a manner that the concentration of fructose in the medium leaving the column is between 40 and 85% especially 75 and 80%. The pH of the reaction medium preferably is in the range 6 to 10 with optimum activity occurring in the region of pH 8 particularly at pH 7.8 but varying somewhat with every species of enzyme, the preceding values relating to enzyme derived from Arthrobacter organisms. The operating temperature is preferably within the range 50° to 100° C, particularly within the range 45° to 80° C. The pH of the eluate is in general lower than that of the feed because of the product fructose complexing with the oxyanion.

Besides glucose and various species of germanate ions the reaction medium suitably contains the following constituents present in the following proportions:

$Mg^{2+}$, ions at concentrations of about 4 mM — with chloride ions of equivalent concentration and NaOH for adjustment of pH For other enzyme reactions (eg phosphogluociosomerase which converts glucose 6-phosphate to fructose 6-phosphate and where increased yields of the product have been found at 25° C in the presence of species of germanate) the reaction conditions will be very different and must be optimised for each enzyme. Glucose isomerase can also be used to convert D-xylose to D-xylulose and is a suitable candidate for this technology and germanate displaces the equilibrium in favour of increased xylulose yields.

Use of germanate ions as the complexing reagent has advantages over the use of borate compounds suggested previously in that germanate species form strong complexes with fructose and are more selective than borate stereo chemically in sugar complexing. The toxicity problems associated with the use of borate compounds are avoided. Unlike areneboronic acids, germanate can form a 1:2 germanate-fructose chelate so economising on the use of complexing agent.

The normal optimum pH of the enzyme alone may not be the optimum pH for the combined enzyme/complexing reagent process. Thus any ability to lower the optimum pH of an enzyme, eg of glucose isomerase from pH 8.5 to pH 7, will be beneficial in reducing the costs of removing the colour produced during the enzyme process. This is unexpectedly true in the case of Arthrobacter glucose isomerase and may be true with other important enzymes. Equally the ability to reduce the operating temperature and yet attain the same percentage-conversion in the same operating time will also be beneficial. While this is not the case with Arthrobacter glucose isomerase it is possible to save operating time because of another unexpected advantage. The addition of germanate markedly increases the initial reaction rate of conversion of glucose to fructose so that economic conversions are obtainable with a shorter residence time. Further it is fortunate that germanate causes no destabilising effect on the Arthrobacter glucose isomerase over the time studied providing the pH fall accompanying the production of fructose in the presence of germanate is ameliorated.

EXAMPLE 1

Enzymatic Conversion of Glucose to Fructose

A series of aqueous glucose solutions containing different concentrations of glucose together with magnesium ions and germanate ions were passed through a column 32 cms in length and 0.4 cms internal diameter packed with flocculated whole cells containing glucose isomerase. Corresponding solutions containing no germanate were also passed through the column for the purpose of comparison. The percentage conversion of glucose to fructose in the eluate from the column was measured on the Autoanalyser using the resorcinol method. The reactions were carried out at an initial pH of 8.5 and at a temperature of 60° C, there being a concentration of 0.004M magnesium chloride in the aqueous glucose solutions.

For the preparation of glucose solutions up to 100 mM, in order to prevent the germanate ions causing precipitation of magnesium from the solutions, solutions containing the germanate ions were always added to the glucose solutions entering the column before the magnesium chloride since magnesium is not precipitated by the glucose-germanate complex which forms in the solutions. The solutions containing germanate ions were prepared by suspending germanium dioxide in water, adding a concentrated alkaline solution until pH 10.5 is reached and thereafter adding glucose solution followed by magnesium chloride. On final adjustment to pH 8.5 the solution became clear.

For substrate solutions containing 200 mM germanate or more the germanium dioxide was added to 1M glucose solution so that on addition of alkali intermittently to pH 8.5 the germanate went slowly into solution. A slightly cloudy solution was obtained after adding magnesium chloride but the eluate from the column was perfectly clear.

The results are set out in Table 1.

TABLE 1

| Glucose Concentration (mM) | Germanate ions Concentration (mM) | % Conversion of glucose to fructose | pH of eluate | Flow rate (ml/min) |
|---|---|---|---|---|
| 0.528 | 0 | 59 | n.a. | 0.12 |
| 0.528 | 25 | 75 | n.a. | 0.12 |
| 4.65 | 0 | 57 | 8.3 | 0.10 |
| 4.58 | 25 | 82 | 8.1 | 0.10 |
| 122 | 0 | 47.5 | 7.0 | 0.11 |
| 118 | 25 | 80.5 | 6.8 | 0.11 |
| 337 | 0 | 44.5 | 6.8 | 0.11 |
| 270 | 25 | 63 | 6.7 | 0.11 |
| 259 | 0 | 46+ | 6.5 | 0.11 |

TABLE 1-continued

| Glucose Concentration (mM) | Germanate ions Concentration (mM) | % Conversion of glucose to fructose | pH of eluate | Flow rate (ml/min) |
|---|---|---|---|---|
| 265 | 25 | 53 | 6.3 | 0.11 |
| 300 | 50 | 52 | 6.0 | 0.11 |
| 284 | 100 | 59.5 | 6.4 | 0.11 |
| 275 | 200 | 72.5* | 7.2 | 0.11 |

+55.5% at equilibrium
*82% at equilibrium (final pH 6.5)

As can be seen from Table 1 in each case where comparison solutions containing no germanate ions were tested the fructose concentration was increased in the presence of germanate ions.

EXAMPLE 2

Enzymatic Conversion of Glucose to Fructose

The procedure of Example 1 was repeated using a column of similar dimensions (ie 30 cms in length and 0.4 cms internal diameter) in order to study the effect of higher glucose concentrations. In this case the flow rate was reduced to 0.03 ml/min in order to give a maximum residence time of 125 minutes to attain equilibrium over several hours and the equilibrium value for this set of conditions was recorded. The glucose concentration was always assayed after the mixture had been made to correct for dilution with alkali/magnesium salts.

The results are set out in Table 2.

TABLE 2

| Initial glucose concentration (% w/v) | Germanate ions concentration (mm) | % Fructose (w/v) | % Conversion |
|---|---|---|---|
| 47.4 | 0 | 25.6 | 54.0 |
| 45.6 | 364 | 32.0 | 70.0 |
| 43.7 | 524 | 35.0 | 80.0 |
| 43.5 | 696 | 36.5 | 84.0 |
| 50.0 | 800 | 39.7 | 79.4 |

As can be seen from the results the presence of germanate ions greatly increased the % conversion to fructose.

Fructose was assayed by the Chaplin-Kennedy method (Carbohydrate Res., 1975, 40, 227–33). This method tends to give higher results than the resorcinol method which was used in all subsequent examples for fructose.

In a further experiment assayed by the resorcinol method (Carbohydrate Res., 26, (1975) 41) using a column of the same dimensions at 60° and pH 8.5 the following results were obtained using different flow rates on the column.

| Flow rate (ml/min) | COLUMN (with added 4mM MgCl) | FEEDS |
|---|---|---|
| | 51.2% w/v glucose only | 47.8% w/v glucose + 800mM germanate |
| 0.015 | 53 | 74 |
| 0.030 | 42.5 | 69 |
| 0.050 | 36 | 50 |
| | % conversions to fructose | |

The product from the initial glucose concentration of 43.5% in Table 2 above was fractionated on the Jeol Ltd anion exchange resin in the borate form using a gradient elution with borate buffers (0.13M borate pH7 to 0.35M borate pH 9.8) to effect a separation between the glucose and fructose in the product. The same separation was also performed after removal of the germanate on a column of "BORASORB" (registered Trade Mark, see previously). The ratio of fructose to glucose was 3.31 : 1 without prior removal of germanate. Fructose and glucose were assayed using the cysteine-sulphuric acid method.

EXAMPLE 3

Chemical Conversion of Glucose to Fructose

The purely chemical conversion of glucose to fructose in the presence of germanate ions was assessed by heating a solution containing 50% w/v glucose, 4mM magnesium salt and 600 mM germanate ions to 60° C at pH 8.5. The fructose concentrations found after various times were as follows.

| Time (Min) | % Fructose |
|---|---|
| 90 | 3.3 |
| 135 | 4.6 |
| 180 | 5.7 |

The experiment was repeated at 90° C with a glucose concentration of 48.4–50% w/v and a germanate concentration of 600mM–582mM. The % conversions to fructose obtained after various times are set out in Table 3. Fructose was assayed by the resorcinol method. Nitrogen was present in the heated syrup throughout the course of the experiment. In all cases the initial pH which had been measured at 31° C fell and was readjusted to the original pH at the time stated.

TABLE 3

| 48.4% w/v glucose Initial pH 7.0 No added MgCl$_2$ 582mM Germanate | | 50% w/v glucose Initial pH 7.5 No added MgCl$_2$ 600MM Germanate | | 50% w/v glucose Initial pH 8.0 No added MgCl$_2$ 600mM Germanate | |
|---|---|---|---|---|---|
| Time (hr) | % Conversion to fructose | Time (hr) | % Conversion to fructose | Time (hr) | % Conversion to fructose |
| 0.5 | 2.0 | 0.5 | 4.3 | 0.5 | 9.1 |
| 1.0 | 3.8 | 1.0 | 8.2 | 1.0 | 12.5 |
| 1.5 | 4.7 | 1.5 | 9.7 | 1.5 | 14.4 |
| 2.5 | 6.8 | | | 2.0 | 15.2 |
| 3.0 | 7.4 | 3.0 | 12.0 | 3.0 | 15.45 |
| 3.5 | 7.8 | 3.5 | 12.6 | 3.5 | 15.4 |
| | | | | | (pH 6.74) |
| 4.0 | 8.3 | | | 4.0 | 18.3 |
| 4.5 | 8.7 | 6.0 | 12.2 | 4.5 | 18.3 |
| | | (final pH 6.37) | | | |

Similar experiments were carried out in the presence of added MgCl$_2$. Results obtained by the resorcinol method are given in Table 4.

The following results obtained with 1.245M glucose, 600mM germanate and 4mM MgCl$_2$ heated at pH 8.5 and 90° illustrate the importance of the ratio of glucose : germanate.

| Time (hr | 0.5 | 1.0 | 1.5 | 2.0 | 2.5 | (pH 7.48) |
|---|---|---|---|---|---|---|
| % Conversion to fructose | 19.8 | 31.6 | 36.2 | 38.6 | 38.6 | |
| Time (hr) | 3.66 | 4.33 | 6 | 6.5 | | |
| % Conversion to fructose | 46.1 | 48.5 | 48 | 45 | | |

The product obtained a few hours subsequently was separated (with and without the prior removal of germanate) on a borate column. Virtually identical values of 39.7% fructose were obtained eluting at the calibrated position for fructose.

TABLE 4

| 50% w/v glucose Initial pH 8 0.004 M MgCl$_2$ 600mM Germanate | | 50% w/v glucose Initial pH 8.5 0.004 M MgCl$_2$ 600mM Germanate | | 50% w/v glucose Initial pH 9.0 0.004 M MgCl$_2$ 600mM Germanate | |
|---|---|---|---|---|---|
| Time (hr) | % Conversion to fructose | Time (hr) | % Conversion to fructose | Time (hr) | % Conversion to fructose |
| | | 0.5 | 19.5 | 0.5 | 30.3 |
| | | 1.0 | 28.5 | 1.0 | 35.2 |
| 2.17 | 16.9 | | | 2.0 | 35.7 |
| 2.83 | 19.0 | 2.83 | 29.8 | 2.33 | 36.7 |
| 3.33 | 18.8 | 3.33 (pH 6.42) | 27.2 | 2.67 (pH 6.98) | |
| 4.0 (pH 6.37) | 18.0 | | | 3.33 | 35.8 |
| 4.5 | 22.1 | 4.5 | 34.3 | 3.67 | 36.2 |
| 4.83 | 23 | 5.0 | 35.5 | | |
| 5.33 | 22.7 | | | | |

A 55% w/v glucose, 600mM germanate, 0.004 M MgCl$_2$ solution heated at 90° and of initial pH 7.5 after 6 hours showed a 13.7% conversion to fructose as assayed by the resorcinol method.

The chemical conversion of glucose to fructose proceeded very slowly at low germanate concentrations at 90° and pH 8.5 with no added magnesium chloride.

| 100mM glucose 10mM germanate | | 20mM glucose 10mM germanate | | 20MM glucose 20mM germanate | |
|---|---|---|---|---|---|
| Time | % Conversion | Time | % Conversion | Time | % Conversion |
| 0.5 | 3.5 | 0.5 | 4.3 | 0.5 | 4.3 |
| 1 | 7.6 | 1 | 8.5 | 1 | 8.5 |
| 1.5 | 10.7 | 1.5 | 11.7 | 2 | 15.5 |
| 2.67 | 18.2 | 2.5 | 18.7 | | |
| 3+ (pH 8.16) | 18.8 | 3+ (pH 7.78) | 19.8 | | |
| 3.5 | 21.5 | 3.5 | 25.3 | 3+ (pH 8.22) | 19.8 |
| 4 | 24.2 | 4 | 29.1 | 3.5 | 20.4 |
| | | | | 4 | 25.6 |
| 4.5 | 25.6 | | | | |
| 5 | 27.5 | 5+ (pH 7.8) | 33.4 | 5 | 29.7 |
| 5.5 | 29.1 | | | 5.8+ (pH 8.0) | 32.2 |
| 6 | 30.3 | 6 | 36.8 | 6 | 33.5 |
| 7 | 31.8 | | | 7 | 37.3 |
| 7.5+ (pH 7.82) | 31.9 | 7.5 | 39.7 | | |
| 8.5 | 33.4 | 8 | 40.6 | 8 | 39.4 |
| 9 | 34.6 | 9 | 40.6 | 9 | 38.9 |

+pH adjusted to 8.5

EXAMPLE 4

Conversion of Glucose to Fructose Using Soluble Glucose Isomerase

The initial reaction rates using glucose isomerase in a soluble form (200μl) were investigated at 60° and pH 8.5 with substrate D-glucose at 0.5 mM and added 4mM MgCl$_2$ and 0.5 mM CoCl$_2$ constant in a series of solutions (25 ml) containing different amounts of added germanate. The solutions were assayed with the automated resorcinol method.

None, 6.25μg fructose/min/ml enzyme
0.5mM germanate, 8.75μg fructose/min/ml enzyme
25mM germanate, 15μg fructose/min/ml enzyme
The % conversion to fructose after 21 hours was also assessed. None, 43% conversion; 0.5mM, 51% conversion; 25mM, 62% conversion.

EXAMPLE 5

Conversion of Mannose to Fructose

A solution containing 50% w/v mannose, 4mM $MgCl_2$ and 600 mM germanate was heated at 90° C and pH 8.5. The concentrations of fructose assayed by the resorcinol method are set out in Table 5.

Table 5

| Time (min) | | % Conversion to fructose |
|---|---|---|
| 30 | | 3.44 |
| 60 | | 6.42 |
| 120 | | 13.4 |
| 150 | | 15.4 |
| 170 | (pH 7.25 readjusted to pH 8.5) | 15.9 |
| 260 | | 20.4 |
| 280 | | 20.6 |

EXAMPLE 6

Conversion of Glucose-6-phosphate to Fructose-6-phosphate

Using the technique of Example 1 a series of experiments was performed using a 0.5 mM solution of glucose-6-phosphate to which different amounts of germanate ions were added. The experiments were carried out at 25° and at a series of different pH values. The enzyme used was Sigma Grade III from yeast (crystalline suspension) and was diluted 200 times and dialysed against distilled water to remove buffer salts before use. Fructose-6-phosphate produced was assayed by the resorcinol method.

The percentage conversions obtained are set out in Table 6.

TABLE 6

| Germanate ions concentration (mM) | % Conversion | | | | | | | |
|---|---|---|---|---|---|---|---|---|
| | pH 10.5 | pH 10.0 | pH 9.5 | pH 9.0 | pH 8.5 | pH 8.0 | pH 7.5 | pH 7.0 |
| 200 | 84 | 86 | 84 | 63 | 56 | 48 | 36 | 30 |
| 100 | 81 | 81 | 77 | 68 | 48 | 40 | 36 | 32 |
| 50 | 82 | 81 | 77 | 62 | 48 | 40 | 33 | 29 |
| 25 | 89 | 81 | 78 | 60 | 50 | 39 | 29 | 23 |
| 12.5 | 76 | 69 | 64 | 56 | 40 | 29 | 25 | 22 |
| 6.25 | 62 | 55 | 48 | 40 | 32 | 25 | 23 | 22 |
| 0 | | | | | 23 | | | 22 |

As can be seen the % Conversion increased in the presence of germanate ions.

EXAMPLE 7

Enzymatic Conversion of Glucose to Fructose — stability

A feed solution containing 41.2%, glucose 600mM germanate and 4mM magnesium chloride at an initial pH of 7.0 was passed continuously through an enzyme column similar to that of Example 1. The final pH and % conversion to fructose were measured after various intervals of time. The experiment was divided into three periods.

After a first period of 43 hours the feed solution was clarified by sintered filtration to remove the slight precipitate which tends to form in glucose/germanate solutions after lengthy periods. This led to a rise in activity which had been falling slightly. After a second period extending from 43 to 102 hours the feed pH was increased to 7.8 with beneficial results. The pH of the eluate tends to fall markedly after prolonged passage through the column. It appears that conversions in excess of 70% can be maintained over a prolonged period if the pH of the column eluate is not allowed to fall significantly below 7.0. The results are set out in Table 7A.

TABLE 7A

| Time | Initial pH | Final pH after passage through enzyme reactor | % conversion to fructose |
|---|---|---|---|
| 2 hrs | 7.0 | 6.6 | 67.2 |
| 17 hrs | 7.0 | 5.6 | 61.5 |
| 43 hrs | 7.0 | 5.5 | 60.8* |
| 54 hrs | 7.0 | 5.8 | 64.9 |
| 102 hrs | 7.0 | 5.7 | 65.5** |
| 126 hrs | 7.8 | 6.9 | 76.5 |
| 150 hrs | 7.8 | 6.9 | 78.3 |
| 174 hrs | 7.8 | 6.9 | 76.5 |
| 198 hrs | 7.8 | 6.8 | 71.6 |

*End of first period — feed solution then clarified
**End of second period — initial pH then raised The effects of different temperatures on stability was measured using an enzyme column the same as that used above. The results are set out in Tables 7B and 7C. Reaction conditions are given at the heads of the Tables. In Table 7B the conversion is that achieved at equilibrium whilst in Table 7C the conversion is that achieved initially. In both Tables 7B and 7C the results show the cumulative effect.

TABLE 7B

44% w/v Glucose + 4mM $MgCl_2$ + 600mM germanate pH 7.1 at a flow-rate of 0.05 ml/min through the enzyme

| Temp ° C | Date | % Conversion to Fructose (enzyme washed 2 days ago) |
|---|---|---|
| 55 | 26.11.75 | 69.2 |
| 60 | 26.11.75 | 73.4 |
| 65 | 26.11.75 | 75.1 |
| 70 | 27.11.75 | 71.5 |
| 75 | 27.11.75 | 72.1 |
| 80 | 27.11.75 | 75.0 |
| 85 | 27.11.75 | 60.5 |

TABLE 7C

44% w/v Glucose + 4mM $MgCl_2$ + 600mM germanate pH 7.1 at a flow-rate of 0.16 ml/min through the enzyme

| Temp ° C | Date | % Conversion to Fructose (enzyme washed 14 days ago) | Time through column at a particular temperature (hrs) | Cumulative time solution has passed through column (hrs) |
|---|---|---|---|---|
| 55 | 8/12/75 | 22.7 | 1½ | 1½ |
| 60 | 9/12/75 | 30.1 | 1½ | 3 |
| 65 | " | 31.8 | 1½ | 4½ |
| 70 | " | 34.1 | 1½ | 6 |
| 75 | " | 35.8 | 2½ | 8½ |
| 80 | " | 32.4 | 2 | 10½ |
| 85 | " | 25.6 | 1½ | 12 |

EXAMPLE 8

Chemical Conversions of Sugars a. Glucose to Fructose

Glucose solutions (55–60 w/v) were prepared both with and without inclusion of 600mM germanate at pH 12 at 20° C. Immediately after preparation 50µl aliquots were taken, diluted to 5 ml and then stored at a temperature of −20° C until required for analysis. The syrups were then placed in stoppered flasks in a refrigerator at 4.5° C. The flasks were shaken daily and aliquots were removed at the time intervals shown in Table 8A. All samples were analysed by separation on an ion exchange resin with borate and the peaks were monitored by the automated cysteine/sulphuric acid assay (Anal Biochem., 26, (1968) p219). It was noted that the germanate containing solution developed only a slight off white colour over the whole period covered by Table 8A whilst the germanate free solution rapidly acquired a green colour which intensified throughout the incubation.

The results are given in Table 8A.

TABLE 8A

| Time of storage (days) | Solutions containing germanate | | Solutions without germanate | |
|---|---|---|---|---|
| | Fructose Produced w/v | Glucose remaining w/v | Fructose produced w/v | Glucose remaining w/v |
| 0 | 2.1 | 51.8 | 2.2 | 48.7 |
| 14 | 17.8 | 40.3 | 8.9 | 44.6 |
| 23 | 25.0 | 34.2 | 11.1 | 35.2 |
| 27 | — | — | 11.1** | 35.6 |
| 31 | 31.9* | 26.9 | — | — |

*Equivalent to 54% conversion. Only 3.1% mannose present.
**5% mannose present b. The effect of incubation at pH 12 and 5° C in the presence and absence of germanate ions was investigated with a number of sugars. The results obtained and basic conditions in respect of solutions of fructose, mannose, maltose and 3-O-Methyl D-glucose are set out in Tables 8B, 8C, 8D and 8E respectively. In all cases the presence of germanate has two effects a) it delays destruction of sugars and b) it alters the constitution of the equilibrium mixture. In the Tables the figures do not add up to 100% because of decomposition.

TABLE 8B

| Initial D-Fructose concentration Germanate | 52.1% w/v None | | 50.5% w/v 600 mM |
|---|---|---|---|
| Components Found (%) | 17 days | 30 days | 17 days |
| D-Glucose | 36.4 | 42.3 | 18.1 |
| D-Mannose | 22.8 | 24.3 | 26.7 |
| D-Fructose | 27.8 | 21.2 | 51.2 |
| Unknown a | +++ | +++ | + |
| Unknown b | ++++ | ++++ | + |

TABLE 8C

| Initial D-Mannose concentration Germanate | 51.14% w/v None | | 53.3% w/v 600 mM | |
|---|---|---|---|---|
| Compounds found (%) | 17 days | 30 days | 17 days | 30 days |
| D-Mannose | 79.3 | 53.4 | 60.2 | 27.45 |
| D-Fructose | 13.65 | 18.3 | 32 | 44.4 |
| Unknown 1 | + | ++ | — | — |
| Unknown 2 | + | +++ | — | — |
| D-Glucose | 7.2 | 18.8 | 7.1 | 13.36 |

TABLE 8D

| Initial Maltose concentration Germanate | 59% w/v None | | 58.7% w/v 358mM | |
|---|---|---|---|---|
| Compounds found (%) | 15 days | 27 days | 15 days | 27 days |
| Maltose | 38.3 | 26.5 | 48.5 | 13.9 |
| Maltulose* | 24.5 | 21.5 | 51.9 | 67.9 |
| Fructose | 2.4 | 4.39 | — | ++ |

TABLE 8D-continued

| Initial Maltose concentration Germanate | 59% w/v None | | 58.7% w/v 358mM | |
|---|---|---|---|---|
| Compounds found (%) | 15 days | 27 days | 15 days | 27 days |
| Glucose | 22.1 | 22.8 | trace | 9.3 |

*calculated as M.Wt. with 0.5 molar glucose response + 0.5 molar fructose response.

TABLE 8E

| Initial 3-O-Methyl D-glucose* concentration Germanate | 41.8% w/v None | 58.7% w/v 464 mM |
|---|---|---|
| Components found (%) | 15 days | 15 days |
| 3-O-methyl fructose** | 18.5 | 29.7 |
| 3-O-methyl glucose | 36.1 | 46 |

*known to be very alkali labile
**calculated with reference to fructose response

EXAMPLE 9

Enzymic Conversion of Xylose to Xylulose

A solution of xylose was made up containing 44% w/v xylose and 4mM $MgCl_2$ at pH 7.0 and was passed through the glucose isomerase enzyme column used in the previous examples for the enzymic conversion of glucose to fructose (Column temp = 60° C and flow rate = 0.05 ml/min). In a similar manner a solution containing 44% xylose, 4mM $MgCl_2$ and 600 mM germanate ions was passed through the column at pH 7.0.

After 2 hours the fractions were collected and separated on an ion exchange resin in the borate form. A control xylose standard was also passed down the column as a comparison. An automate version of the cysteine/$H_2SO_4$ assay for pentoses was used to analyse the peaks in the order they cameoff the column. The assay also reacts with pentuloses and the product xylulose from the xylose solutions that had been passed through the enzyme column was clearly visible.

Because a standard xylulose for calibration purposes is not yet available the extent of the reaction was ascertained by comparing the areas under the peaks. This ratio of xylulose formed from total xylose and xylulose was 41:100 but with germanate ions present the ratio was 58 : 100.

EXAMPLE 10

Conversion of Glucose to Fructose Using Stannate Ions

Two feed solutions containing 44.6% glucose and 4mM $MgCl_2$ at pH 8.5 were passed through the glucose isomerase enzyme column used in previous examples. One solution contained no stannate ions whilst the other contained 600mM stannate ions obtained from crystalline $Na_2SnO_3.3H_2O$. The results are shown in Table 9.

TABLE 9

| Time (hrs) | % Conversion to Fructose No Stannate | % Conversion to Fructose (600mM Stannate) | |
|---|---|---|---|
| | | (a) | (b) |
| 1 | — | — | 59.4 |
| 2 | — | — | 56.6 |
| 3 | 42.6 | 53.3 | — |
| 4 | — | — | 56.1 |

Samples from the reactor column eluate, when mixed with additional glucose did not produce further fructose indicating that active glucose isomerase had not been leached from the reactor column.

EXAMPLE 11

Enzymic Conversion of Glucose to Fructose : Effect of pH and Germanate Levels a. Two series of experiments were performed using a glucose isomerase column (length 31 cm, diameter 4 cm) similar to that used in earlier examples. Each series compared results obtained using feed solutions comprising glucose and 4mM $MgCl_2$ with and without 600mM germanate. The flow rate through the column was 0.05 ml/min and the temperature of the enzyme was 60° C. The initial pH of the feed solutions was varied between different experiments in each series and the final pH of eluate was measured. The results are set out in Table 10.

TABLE 10

| Series | Initial Feed pH | Order of analysis | Initial % glucose concn (w/v) | Germanate concn. mM | % conversion to fructose | Final pH of eluate |
|---|---|---|---|---|---|---|
| 1 | 7 | 3 | 48 | 0 | 48.2 | — |
| 1 | 6.9 | 8 | 47 | 0 | 49.6 | 7.2 |
| 1 | 8.5 | 1 | 49.2 | 0 | 49.2 | — |
| 1 | 8.5 | 2 | 49.3 | 0 | 49.2 | — |
| 1 | 7 | 5 | 40.2 | 600 | 76.5 | 7.0 |
| 1 | 7 | 6 | 40.0 | 600 | 70.3 | 6.9 |
| 1 | 8.5 | 4 | 38.2 | 600 | 74.6 | 7.2 |
| 1 | 8.3 | 7 | 40.0 | 600 | 72.5 | 6.6 |
| 1 | 8.3 | 9 | 37.0 | 600 | 71.2 | 7.0 |
| 2 | 7.0 | 2 | 42.0 | 0 | 54.0 | 6.8 |
| 2 | 8.4 | 1 | 41.6 | 0 | 49.3 | 7.1 |
| 2 | 8.5 | 4 | 44.6 | 0 | 54.9 | 7.0 |
| 2 | 7.1 | 5 | 53.4 | 600 | 67.4 | 6.8 |
| 2 | 8.6 | 3 | 50.0 | 600 | 66.7 | 6.8 | b. Two series of experiments were performed using a glucose isomerase column similar to that used in earlier examples. The feed solutions comprised 50 w/v nominal glucose concentration, 4mM $MgCl_2$ and 200 and 600 mM germanate respectively in the different series. The experiments were performed at a variety of pH values. A comparative series of experiments was performed using solutions containing no germanate. In all the experiments the solutions were pumped through the column of immobilized enzyme at a flow rate of 0.05 ml/min (75 min nominal residence time). The results are shown in Table 11.

TABLE 11

| pH | Eluate Composition (% Fructose) | | |
|---|---|---|---|
| | No germanate | 200 mM germanate | 600 mM germanate |
| 9.0 | 51 | | 68 |
| 8.5 | 51 | 64 | 69 |
| 8.0 | 49 | 59 | 70 |
| 7.5 | 50 | 60 | 70 |
| 7.0 | 50 | 60 | 70 |
| 6.5 | 39 | 59 | 69 |
| 6.0 | | 58 | |

TABLE 11-continued

| pH | Eluate Composition (% Fructose) | | |
|---|---|---|---|
| | No germanate | 200 mM germanate | 600 mM germanate |
| | | 50 | |

EXAMPLE 12

Enzymic Conversion of Glucose to Fructose — Reversibility

Solutions of glucose to fructose having the carbohydrate concentrations shown in Table 12 were prepared. Those solutions to contain germanate were prepared by dissolving weighed amounts of $GeO_2$ in aliquots of these solutions by stirring in small amounts of 50% NaOH solution. Aliquots of $MgCl_2$ solution were added to all these solutions to a final concentrations of 4mM and the pH of all solutions was adjusted to 8.5 at 25° C.

Figure 1:
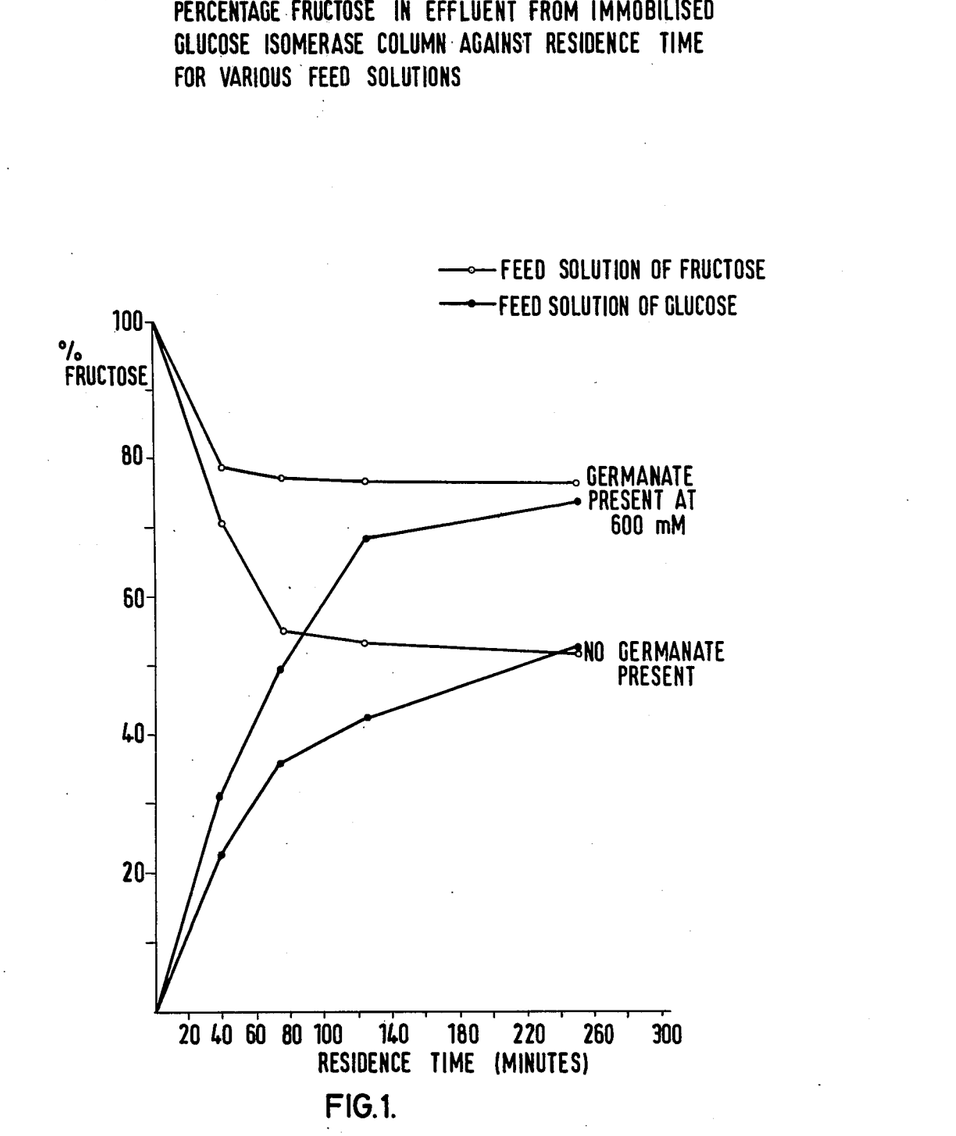
FIG. 1 of the drawings shows the percentage of fructose produced against time in the presence of and the absence of germanate.
Figure 2:
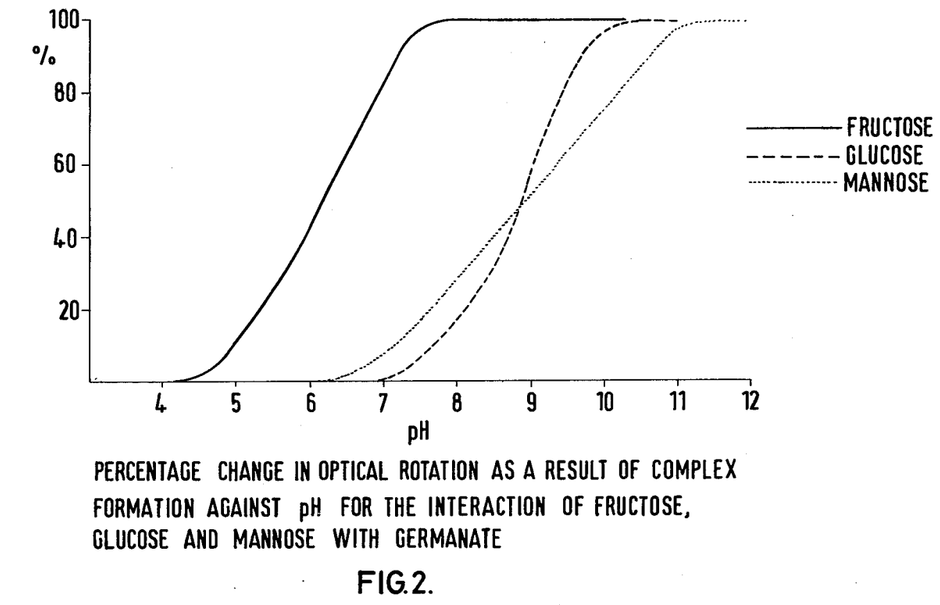
FIG. 2 of the drawings shows the percentage change in optical rotation as a result of complex formation against pH for germanate complexes with glucose, fructose and mannose. As can be seen the fructose complex forms at a lower pH than those of glucose and mannose.

The solution were then pumped at the flow rates shown through the enzyme column (30 × 0.4 cm) at 60° C. The level of fructose in the column eluate was monitored, after dilution. For calibration syrups of 0.55% w/v were prepared and passed through the whole analytical system. To check the initial level of glucose in the feed syrups the samples and the calibration standard syrups were diluted 2 × $10^4$ manually and analysed by the cysteine - sulphuric acid method. The results are set out in Table 12 and are shown graphically in FIG. 1 of the drawings which clearly shows that with no germanate present the equilibrium position is between 52 and 53% fructose whether one starts with a glucose or a fructose feed syrup and is between 74 and 79% in the presence of 600mM germanate, Again starting either from glucose or fructose as the feed syrup.

TABLE 12

| Flow Rate | Carbohydrate feed compsn. % w/v without germanate | Carbohydrate compsn. % w/v with germanate in feed | Nominal Residence time | Eluate composition | | Feed type |
|---|---|---|---|---|---|---|
| | | | | No germanate | 600mM germanate | |
| 0.1 | 54.6 | 50.5 | 38 | 22.5 | 31.0 | |
| 0.05 | 51.2 | 47.8 | 75 | 36.0 | 49.5 | Glucose |
| 0.03 | 51.2 | 47.8 | 125 | 42.5 | 68.5 | |
| 0.015 | 51.2 | 47.8 | 251 | 53.0 | 74.0 | |
| 0.1 | 55.0 | 48.2 | 38 | 71.0 | 79.0 | |
| 0.05 | 55.0 | 48.2 | 75 | 55.5 | 77.5 | |
| 0.03 | 55.0 | 48.2 | 125 | 53.5 | 77.0 | Fructose |
| 0.015 | 55.0 | 48.2 | 251 | 52.0 | 77.0 | |

EXAMPLE 13

Enzymic Conversion of Glucose to Fructose — Concentration Dependence

A series of solutions containing 600mM germanate and 4mM $MgCl_2$ but having differing concentrations of glucose were passed through a column of glucose isomerase similar to that used in previous examples at a temperature of 60° C. The results are shown in Table 13.

TABLE 13

| Glucose feed concentration (% w/v) | % Conversion to Fructose | Final pH |
|---|---|---|
| 20.6 | 92.7 | 7.8 |
| 30.0 | 80.0 | 7.8 |
| 40.0 | 72.5 | 7.5 |
| 53.4 | 67.4 | 6.8* |
| 60.0 | 65.0 | 7.5 |

*From a previous experiment.

EXAMPLE 14

Chemical Conversion of Melibiose

The chemical conversion of melibiose (6 - O - α -D-galactopyranosyl-D-glucose) was studied in the presence and absence of 324mM germanate at pH 12.0 and at 4° C. The concentration of melibiose in the initial solution was 51.6% w/v. The results are shown in Table 14.

TABLE 14

| | % of given sugar in total sugar after no. of days set out at heads of individual columns | | | | |
|---|---|---|---|---|---|
| Compound | 0 | 15 | 29 | 42 | Germanate |
| Melibiose 6-0-α-D | 92.2 | 55.5 | 57.5 | 49.6 | |
| galacto-pyranosyl-D-fructose | 3.2 | 9.8 | 12.8 | 11.0 | Absent |
| Galactose | — | 9.9 | 11.9 | 12.3 | |
| Recovery of identified products | 95.4 | 75.2 | 82.2 | 72.9 | |
| Melibiose 6-0-α-D | — | 42.7 | 35.0 | 25.2 | |
| galacto-pyranosyl-D-fructose | — | 37.8 | 42.5 | 31.1 | Present |
| Galactose | — | — | 7.9 | 12.8 | |
| Recovery of identified products | — | 80.5 | 85.4 | 69.1 | |

We claim:

1. A process for the conversion of an aldose or aldose derivative to a ketose or ketose derivative, comprising:
   forming an aqueous solution containing an aldose or aldose derivative and chemically or enzymatically isomerizing said aldose or aldose derivative to a corresponding ketose or ketose derivative in the presence of a complexing reagent which is an oxyanion or mixed complex oxyanion of germanium or tin which forms a stronger complex with the ketose or ketose derivative than with the aldose or aldose derivative,
   maintaining said aqueous solution under aldose to ketose isomerization conditions, and
   recovering a product enriched in said ketose or ketose derivative.

2. A process for the conversion of an aldose or aldose derivative to a ketose or ketose derivative, comprising:
   forming an aqueous solution containing an aldose or aldose derivative and chemically or enzymatically isomerizing said aldose or aldose derivative to a corresponding ketose or ketose derivative in the presence to a complexing reagent which is an oxyanion or mixed complex oxyanion of germanium which forms a stronger complex with the ketose or ketose derivative than with the aldose or aldose derivative,
   maintaining said solution under aldose to ketose isomerization conditions, and
   recovering a product enriched in the ketose or ketose derivative.

3. A process according to claim 1 wherein mannose or glucose is isomerised to fructose.

4. A process according to claim 1 wherein said isomerization involves the use of an enzyme.

5. A process according to claim 1 wherein mannose or glucose is enzymatically isomerised to fructose with glucose isomerase.

6. A process according to claim 4 wherein the enzyme used in the isomerization is immobilised on a solid matrix which is a living cell, an inactivated cell or any other suitable support.

7. A process according to claim 1 wherein the complexing reagent is introduced into the process as an aldose-oxyanion complex or a derivative of an aldose oxyanion complex or as a salt or an oxide or another compound which forms oxyanions or mixed complex oxyanions under the process conditions.

8. A process according to claim 1 wherein the mixed complex oxyanion is one formed by the interaction of an oxyanion of germanium or tin with an ion of another element from Group IV of the Periodic Table or of an element from Group V or Group VI.

9. A process according to claim 5 wherein the glucose isomerase is derived from a strain of Arthrobacter.

10. A process according to claim 4 wherein the complexing reagent is present in a solution containing the aldose which is passed through a mass containing the enzyme.

11. A process according to claim 1 wherein the ketose produced by the process and/or a mixture comprising the ketose and residual aldose is separated from the complexing reagent and the complexing reagent either alone or together with residual aldose is recycled.

12. A process according to claim 10 wherein glucose is enzymatically isomerized to fructose with glucose isomerase and the complexing reagent is present in the solution in concentrations between 200mM and 800mM.

13. A process according to claim 5 wherein glucose is enzymatically isomerized to fructose with glucose isomerase and the conversion takes place using an aqueous feed solution containing 30% w/w to 50% w/w glucose.

14. A process according to claim 5 which is performed using a reaction medium having a pH in the range 6 to 10.

15. A process according to claim 5 wherein the conversion takes place at a temperature within the range 50° to 100° C.

16. A process according to claim 1 wherein said complexing reagent which is an oxyanion or mixed complex oxyanion of germanium or tin is a germanate.

17. A process according to claim 1 wherein said complexing reagent which is an oxyanion or mixed complex oxyanion of germanium or tin is a stannate.

18. A process according to claim 16 wherein glucose is converted to fructose.

* * * * *